US012636193B2

(12) United States Patent
Frost et al.

(10) Patent No.: US 12,636,193 B2
(45) Date of Patent: May 26, 2026

(54) HEARING PROTECTION DEVICE TESTING SYSTEM AND METHOD

(71) Applicant: LIGHTSPEED AVIATION, INC., Lake Oswego, OR (US)

(72) Inventors: Brian David Frost, Lake Oswego, OR (US); Allan Schrader, Lake Oswego, OR (US)

(73) Assignee: LIGHTSPEED AVIATION, INC., Lake Oswego, OR (US)

( * ) Notice: Subject to any disclaimer, the term of this patent is extended or adjusted under 35 U.S.C. 154(b) by 413 days.

(21) Appl. No.: 18/387,009

(22) Filed: Nov. 3, 2023

(65) Prior Publication Data

US 2024/0148557 A1 May 9, 2024

Related U.S. Application Data

(60) Provisional application No. 63/422,284, filed on Nov. 3, 2022.

(51) Int. Cl.
| | |
|---|---|
| *A61F 11/08* | (2006.01) |
| *A61B 5/12* | (2006.01) |
| *G01H 3/14* | (2006.01) |
| *H04R 1/10* | (2026.01) |
| *H04R 5/033* | (2006.01) |
| *H04R 25/00* | (2006.01) |

(52) U.S. Cl.
CPC .................................... *A61F 11/08* (2013.01)

(58) Field of Classification Search
None
See application file for complete search history.

(56) References Cited

U.S. PATENT DOCUMENTS

| | | | |
|---|---|---|---|
| 3,968,334 | A | 7/1976 | Padilla |
| 5,757,930 | A | 5/1998 | Seidemann et al. |
| 6,567,524 | B1 | 5/2003 | Svean et al. |
| 9,084,060 | B2 | 7/2015 | Liu et al. |
| 9,657,674 | B2 | 5/2017 | Jammoussi et al. |
| 10,190,904 | B2 | 1/2019 | Goldstein et al. |
| 10,337,430 | B2 | 7/2019 | Jammoussi et al. |

(Continued)

FOREIGN PATENT DOCUMENTS

| | | | | |
|---|---|---|---|---|
| CN | 108028974 B | * | 10/2020 | ............. H04R 25/43 |
| CN | 116057962 B | * | 9/2025 | ........... H04R 1/1041 |

*Primary Examiner* — Qin Zhu
(74) *Attorney, Agent, or Firm* — Brooks Kushman P.C.

(57) ABSTRACT

A system and method for testing effectiveness of in-the-ear (ITE) hearing protection devices (HPD) while inserted in a user's ears include a headset having circumaural earcups positionable over the user's ears and programmed to sequentially generate sound at a plurality of frequencies and store the user's hearing threshold at each frequency. The user's values are compared to associated reference values for the ITE hearing protection devices and a processor generates an audio, visual, and/or haptic signal indicative of the ITE HPD effectiveness based on the comparisons. The headset may be used as a secondary or supplemental HPD in combination with the ITE devices. The stored user values at each frequency may be used to automatically compensate ambient sounds for the response of the ITE HPDs and any preexisting user hearing deficiencies to improve speech intelligibility and situational awareness while wearing the devices.

20 Claims, 5 Drawing Sheets

(56)     References Cited

U.S. PATENT DOCUMENTS

| | | | |
|---|---|---|---|
| 10,645,505 B2 | 5/2020 | Voix et al. | |
| 11,263,568 B2 | 3/2022 | Kanukurthy et al. | |
| 2005/0123146 A1* | 6/2005 | Voix ........................ | A61F 11/08 |
| | | | 381/328 |
| 2011/0200217 A1* | 8/2011 | Gurin .................... | A61B 5/123 |
| | | | 381/320 |
| 2014/0254828 A1* | 9/2014 | Ray ........................ | H04R 25/70 |
| | | | 381/103 |
| 2016/0258375 A1 | 9/2016 | Jammoussi et al. | |
| 2016/0374595 A1* | 12/2016 | Henriksen .............. | A61B 5/121 |
| | | | 600/559 |
| 2017/0295269 A1* | 10/2017 | Hosoi .................. | H04R 1/1008 |
| 2020/0214601 A1 | 7/2020 | Brown et al. | |
| 2021/0368258 A1 | 11/2021 | Monsarrat-Chanon et al. | |
| 2024/0225903 A9* | 7/2024 | Kvaløy .................. | A61F 11/14 |

* cited by examiner

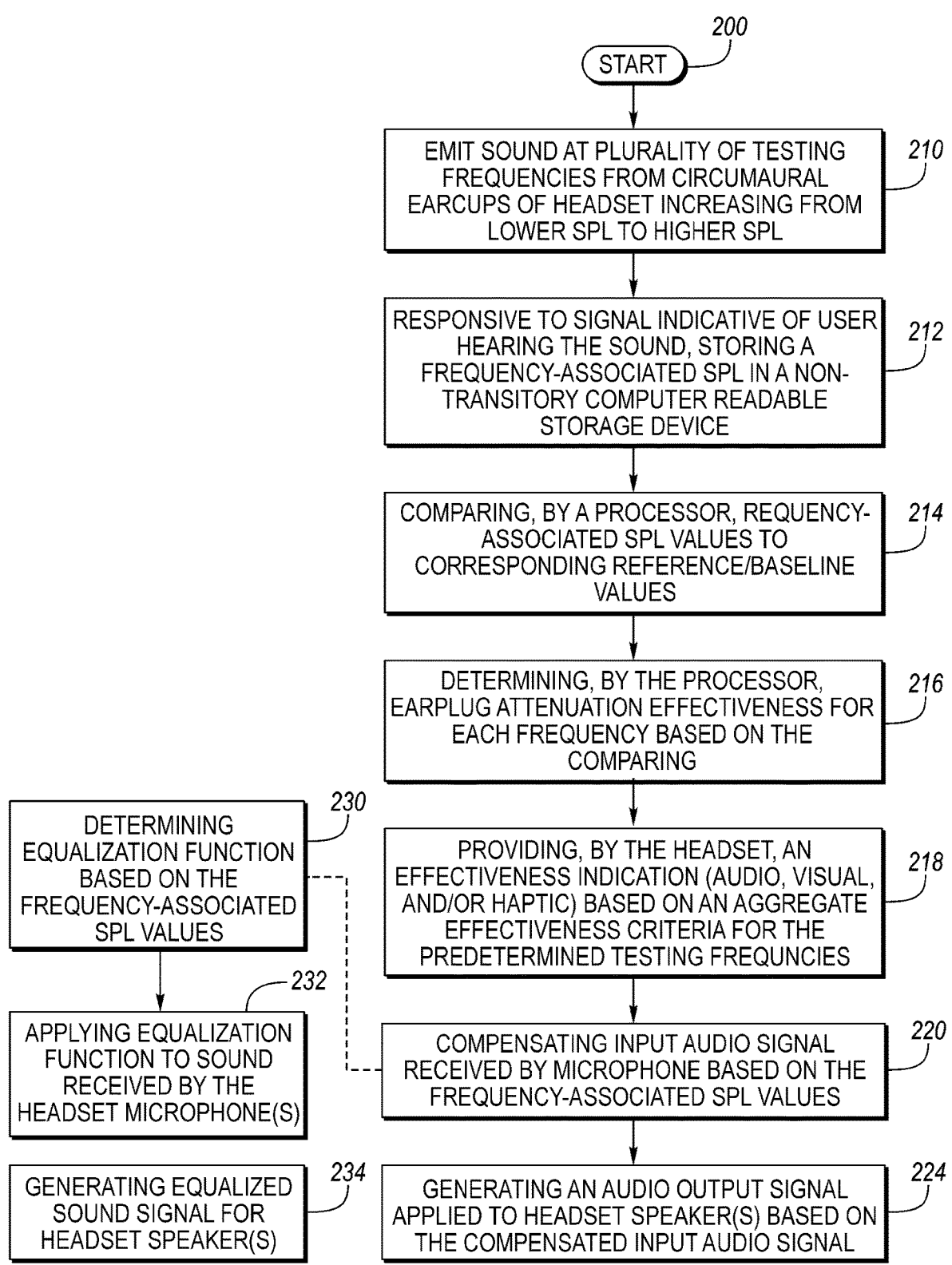

*200*

START

EMIT SOUND AT PLURALITY OF TESTING FREQUENCIES FROM CIRCUMAURAL EARCUPS OF HEADSET INCREASING FROM LOWER SPL TO HIGHER SPL          *210*

RESPONSIVE TO SIGNAL INDICATIVE OF USER HEARING THE SOUND, STORING A FREQUENCY-ASSOCIATED SPL IN A NON-TRANSITORY COMPUTER READABLE STORAGE DEVICE          *212*

COMPARING, BY A PROCESSOR, REQUENCY-ASSOCIATED SPL VALUES TO CORRESPONDING REFERENCE/BASELINE VALUES          *214*

DETERMINING, BY THE PROCESSOR, EARPLUG ATTENUATION EFFECTIVENESS FOR EACH FREQUENCY BASED ON THE COMPARING          *216*

DETERMINING EQUALIZATION FUNCTION BASED ON THE FREQUENCY-ASSOCIATED SPL VALUES          *230*

PROVIDING, BY THE HEADSET, AN EFFECTIVENESS INDICATION (AUDIO, VISUAL, AND/OR HAPTIC) BASED ON AN AGGREGATE EFFECTIVENESS CRITERIA FOR THE PREDETERMINED TESTING FREQUNCIES          *218*

APPLYING EQUALIZATION FUNCTION TO SOUND RECEIVED BY THE HEADSET MICROPHONE(S)          *232*

COMPENSATING INPUT AUDIO SIGNAL RECEIVED BY MICROPHONE BASED ON THE FREQUENCY-ASSOCIATED SPL VALUES          *220*

GENERATING EQUALIZED SOUND SIGNAL FOR HEADSET SPEAKER(S)          *234*

GENERATING AN AUDIO OUTPUT SIGNAL APPLIED TO HEADSET SPEAKER(S) BASED ON THE COMPENSATED INPUT AUDIO SIGNAL          *224*

FIG. 2

HEARING PROTECTION DEVICE TESTING SYSTEM AND METHOD

CROSS-REFERENCE TO RELATED APPLICATION

This application claims the benefit under 35 U.S.C. § 119(e) to U.S. Provisional Application No. 63/422,284 filed Nov. 3, 2022, the disclosure of which is hereby incorporated by reference in its entirety.

TECHNICAL FIELD

This application relates to a system and method for testing in-the-ear (ITE) hearing protection devices, including various types of earplugs, after placement in the ears of a user.

BACKGROUND

In an increasingly noisy world, protecting one's hearing has become a matter of paramount importance. In this regard, in-the-ear (ITE) hearing protection devices (HPDs), including various types of earplugs, have been relied upon as indispensable tools for safeguarding auditory well-being in a wide variety of noisy occupational environments. These unassuming, yet highly effective, devices serve as a shield against the harmful effects of exposure to excessive noise, making them a vital accessory for a wide range of recreational as well as occupational scenarios, such as attending a loud concert, working in a noisy industrial, aerospace, military, entertainment, or tactical ITE HPDs offer a discrete, cost-effective, and efficient solution to help reduce or eliminate hearing loss.

Earplugs and similar ITE HPDs come in various types, each designed to cater to specific needs and preferences. Some examples include foam earplugs made of soft, compressible foam that expands in the ear canal to provide a snug fit provide noise reduction and are often disposable, making them suitable for occasional use. Silicone earplugs are reusable and can be moldable for a customized fit to an individual's ear canal providing a comfortable and effective seal. Flanged earplugs have multiple soft, flexible flanges that create a seal in the ear canal and are commonly used by industrial workers, motorcyclists, and musicians as they offer a balance between comfort and protection. Custom-molded earplugs are individually molded to fit the user's ear canal and may be made by taking an impression of the ear. While custom molded earplugs provide superior comfort and noise reduction, they are more costly to produce and may require trained technicians to for making the impressions and molding the earplugs. High-fidelity earplugs may be designed to reduce noise without distorting sound quality and are often used by musicians and concertgoers to protect their hearing with better sound fidelity. Electronic earplugs and active noise reduction (ANR) or active noise cancellation (ANC) may use a processor to generate a phase-shifted audio signal based on detected ambient noise that combines with noise to reduce or cancel the noise reaching the tympanic membrane. Some of these devices can also amplify ambient sounds, making them valuable for shooting sports, hunting, and professional settings where situational awareness is desired.

Regardless of the type of ITE HPD, proper fit is needed for effective hearing protection, and an improper fit can significantly compromise the ability to reduce noise. When earplugs do not fit correctly, noise leak paths allow sound to bypass the earplugs and reach the ear canal. Proper fit may be influenced by how the user places the earplug in the ear canal in addition to the physical shape and size of the earplugs, which may change after repeated use or with each placement or adjustment by the user. While earplugs are typically designed to provide a specific Noise Reduction Rating (NRR) that indicates the level of noise reduction when properly inserted, improper fitment can significantly reduce the NRR and may lead to unknowing and unintended exposure to harmful noise levels for the user resulting in temporary or permanent noise-induced hearing loss (NIHL).

SUMMARY

Systems and methods according to the disclosure provide a tool for checking earplug insertion effectiveness that can be utilized every time an individual uses earplugs to ensure that the insertion technique provides acceptable attenuation relative to the expected attenuation for a particular type of earplug. The systems and method allow user self-administration of a "hearing test" using a wearable headset having circumaural earcups or muffs after inserting the desired earplugs. The test provides an indication of the earplugs' effectiveness to allow the user to adjust the fitment to achieve a desired indication, such as "acceptable/pass" or "good" for example in contrast to "unacceptable/fail" or "poor" for example. Audio/speech, visual, and/or haptic indications of the test result may be provided to the user. The headset may also be used as a secondary HPD and communication device in combination with the earplugs. Data acquired during the test may be used to generate digital filters to personalize the headset (in combination with the response of the earplugs) equalization, to compensate for hearing deficiencies, and/or to increase speech intelligibility enhancing situational awareness and improving mission effectiveness for various applications.

For earplug insertion loss testing, users may don the ITE HPD testing headset prior to earplug insertion to establish a baseline hearing threshold. After earplug insertion, a second test establishes the attenuation associated with the particular earplugs for a specific insertion placement. The change in measured attenuation represents the specific plug attenuation that a particular insertion has delivered.

In one or more embodiments, a method for testing earplugs positioned within respective ear canals of a user includes emitting a sound at each of a plurality of predetermined testing frequencies from circumaural earcups of a headset configured to be worn by the user, the sound at each of the predetermined testing frequencies increasing from a lower sound pressure level to a higher sound pressure level, responsive to receiving a signal indicative of the user hearing the sound at each of the plurality of predetermined testing frequencies, storing a frequency-associated sound pressure level value in a non-transitory computer readable storage device, comparing, by a processor, the frequency-associated sound pressure level value for each of the plurality of frequencies to corresponding predetermined frequency-associated reference values, determining, by the processor, effectiveness of the earplugs in attenuating sound for each frequency based on the comparing, and providing, by the headset, an indication of the effectiveness of sound attenuation of the earplugs based on an aggregate effectiveness for the predetermined testing frequencies. The method may include the processor performing the increasing from a lower sound pressure level to a higher sound pressure level. The processor may increases the sound pressure level (SPL) in response to a signal from a user operable volume control. The signal indicative of the user hearing the sound may correspond to a signal from the user operable volume control. The signal indicative of the user hearing the sound may correspond to the signal from the user operable volume control, after increasing during a first period of time, either: a) remaining constant for a second period of time, or b) decreasing.

In various embodiments, the method includes providing the indication of the effectiveness of the sound attenuation by providing at least one of a visual, audio, and haptic indication via the headset. The processor may be programmed to determine one or more filters including at least one of a low-pass filter, a high-pass filter, and a band-pass filter to form an equalization function based on the frequency-associated sound pressure level values for at least one of the plurality of frequencies, to apply the equalization function to sound received by at least one microphone of the headset, and to generate an equalized sound signal for at least one speaker of the headset.

In one or more embodiments, the processor may be programmed to compensate an input audio signal received by at least one microphone of the headset based on the frequency-associated sound pressure level values for the plurality of frequencies, and generate an audio output signal applied to at least one speaker of the headset based on the compensated input audio signal.

In various embodiments, the method includes storing the frequency-associated sound pressure level values by wirelessly transmitting the sound pressure level values to a remotely located memory. The remotely located memory may by a wirelessly linked smartphone memory. Alternatively, or in combination, the non-transitory computer readable storage device may comprise removable storage media.

Embodiments may also include a system for evaluating effectiveness of in-the-ear (ITE) hearing protection devices after insertion into ear canals of a user. The system may include a headband configured to extend around the head of the user, a circumaural earcup connected to each end portion of the headband and configured for positioning over an associated ear of the user, an ambient microphone associated with each ear cup and configured to generate signals responsive to ambient sound, an internal microphone positioned within each ear cup and configured to generate signals responsive to sound within a respective earcup, a speaker positioned within each ear cup and configured to generate sound responsive to at least one of a communication signal and the signal from a respective one of the ambient microphones, and at least one processor in communication with the ambient microphones, the internal microphones, and the speakers, the at least one processor. The at least one processor may be programmed to: control the speakers to sequentially generate sound at each of a plurality of frequencies, the sound increasing in sound pressure level (SPL) at each of the plurality of frequencies until receiving a signal responsive to user input, store an SPL value for each of the plurality of frequencies associated with the signal from the user operable input in a memory accessible by the at least one processor, compare each stored SPL value to a corresponding reference value to determine associated difference values, and generate a signal indicative of effectiveness of the ITE hearing protection devices based on the difference values. The system may include a user operable input device configured to generate the signal responsive to the user input. The user operable input device may comprise a wirelessly coupled smartphone, a volume control positioned on one of the circumaural earcups, and/or a keypad positioned on one of the circumaural earcups.

In one or more embodiments, the system includes a boom microphone extending from one of the circumaural earcups and configured to generate signals in response to user speech, the boom microphone in communication with at least one of the speakers and the at least one processor. The system may also include an input jack in communication with the at least one processor and configured to receive an external input/output plug and communicate audio signals between the at least one processor and an external audio device. The system may also include a transceiver in communication with the at least one processor and configured to wirelessly transmit the SPL values to a linked smartphone. In various embodiments, the ambient microphones, the internal microphones, the speakers, and the at least one processor are positioned within at least one of the circumaural earcups.

Embodiments according to the present disclosure may have one or more associated advantages. For example, the system and method provide early detection to validate ear plug insertion and fitment effectiveness with rapid intervention to correct any identified deficiency. Insertion loss data may be subsequently used to enhance communications audio signals to improve intelligibility and/or adjust the audio based on a user's pre-existing hearing loss/deficiencies at particular frequencies. The speed and portability of the ITE HPD effectiveness testing system and method facilitate checking earplug insertion every time an individual uses earplugs to ensure that their insertion technique provides acceptable attenuation based on expected attenuation for the particular type of earplugs.

The above advantages and other advantages and features will be readily apparent from the following detailed description when taken in connection with the accompanying drawings.

BRIEF DESCRIPTION OF THE DRAWINGS

FIG. 2 is a flowchart illustrating operation of a system or method for evaluating ITE HPD effectiveness.

DETAILED DESCRIPTION

Figure 1:
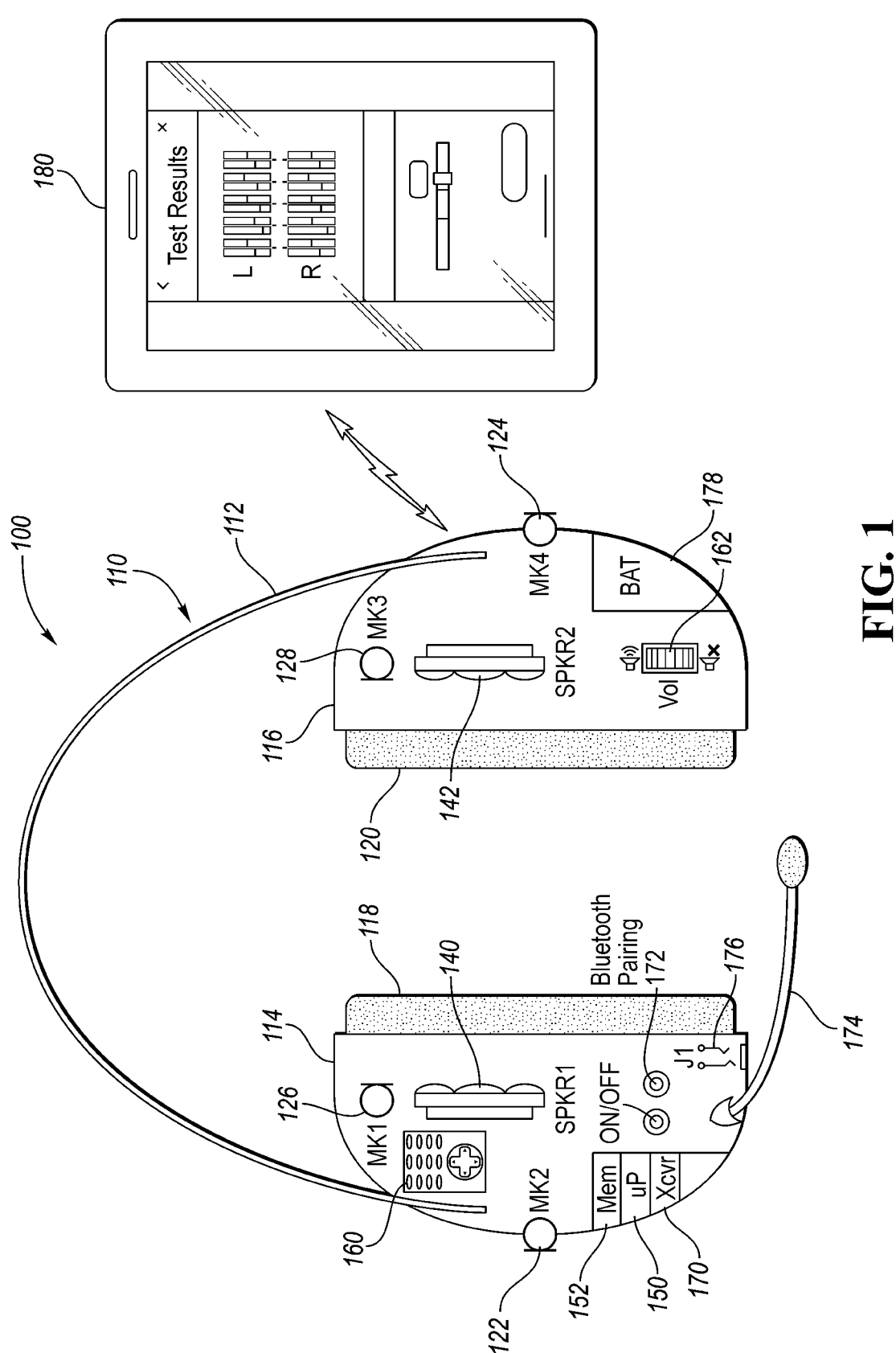
FIG. 1 illustrates a representative system for evaluating effectiveness of in-the-ear (ITE) hearing protection devices after insertion into ear canals of a user.

As required, detailed embodiments are disclosed herein; however, it is to be understood that the disclosed embodiments are merely exemplary and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the teachings and representative embodiments of the disclosure.

According to one aspect, a system or method according to the disclosure includes one or more computers or controllers having a programmed processor that executes instructions stored in a non-transitory computer readable storage medium to perform one or more steps of the method. In general, the processes, methods, or algorithms disclosed herein can be performed by a processing device, general-purpose microprocessor, controller, or computer, which can include any existing programmable electronic control unit or dedicated electronic control unit or controller. Similarly, the processes, methods, or algorithms can be stored as data and instructions in a non-transitory storage medium executable by a controller or computer in many forms including, but not limited to, information permanently stored on non-writable storage media such as ROM devices and information alterably stored on writeable storage media including solid-state, electronic, magnetic, and/or optical storage devices. Certain processes, methods, or algorithms may also be implemented in a software executable object. Alternatively, the processes, methods, or algorithms can be embodied in whole or in part using suitable dedicated or custom hardware components, such as Application Specific Integrated Circuits (ASICs), Field-Programmable Gate Arrays (FPGAs), state machines, controllers, or any other hardware components or devices, or a combination of hardware, software and firmware components. Processing of sound/noise signals may be performed by a programmed commercially available digital signal processor (DSP) in one or more embodiments.

Illustration or description of a process, algorithm or function in a particular sequence or order or by a particular processor, computer, or controller may not be required to perform the described operation or achieve the described result. Some processes, functions, algorithms, or portions thereof may be repeatedly performed, performed in a different sequence, or omitted for particular applications whether or not explicitly illustrated or described as such. In addition, references to processes, functions, algorithms, or portions thereof performed by at least one controller or computer do not imply or require that the same controller or computer perform all of the indicated steps where two or more controllers or computers are provided. Various processes, functions, algorithms, or portions thereof may be performed by a local on-board controller or processor and/or by a remote computer, controller, or processor and communicated to one or more other computers, processors or controllers. to implement various types of processing strategies including interrupt-driven, sequential, parallel, multi-threading, etc.

For best hearing protection, proper sizing and insertion techniques should be used for the specific type of earplugs being used. For foam earplugs, this may involve rolling or molding the earplugs to fit comfortably in the ear canal and holding in place while the foam expands to ensure a secure seal. In some cases, custom-molded earplugs that are individually tailored to the wearer's ear canal can provide the most effective and comfortable protection, although these have various disadvantages with respect to cost and availability, particularly for occasional use. Poor fitment associated with a particular insertion may introduce noise leak paths and reduce the effectiveness of the ITE HPDs resulting in temporary or permanent noise-induce hearing loss (NIHL).

As described in greater detail herein, the present inventors have developed a technique to allow individuals to take a self-administered "hearing test" using a muff-type headset with circumaural earcups after insertion of their ITE HPDs. An onboard or linked application controls generation of a tone at different test frequencies (in sequence) to determine a user hearing threshold at each frequency. In addition to testing effectiveness of the ITE HPDs, the headset may be worn as a supplemental hearing protection device to provide additional passive and/or active attenuation. The corresponding sound pressure levels (SPL) measured during the test may be used by the application to generate filters to personalize the headset equalization, compensating for hearing deficiencies and increasing speech intelligibility of pass-through ambient speech and/or electronic communications to enhance situational awareness and mission effectiveness.

To measure insertion loss for a particular ITE HPD, users wear the testing headset/HPD prior to insertion of the ITE HPDs to take a test establishing a baseline hearing threshold. The headset is then removed and the user inserts the ITE HPDs and dons the headset again to initiate a second test that establishes the attenuation the plugs provide. The change in measured attenuation represents the specific plug attenuation for the particular insertion. The measurement results may be compared to reference values to provide an indication of the effectiveness for the particular insertion to the user so that any deficiencies may be addressed prior to any potential hearing harm associated with ineffective hearing protection.

FIG. 1 illustrates a representative system for evaluating effectiveness of in-the-ear (ITE) hearing protection devices after insertion into ear canals of a user according to various embodiments of the disclosure. System 100 includes a muff-type headset 110 having a headband 112 configured to extend around the head of a user. A circumaural earcup 114, 116 is connected to each end portion of the headband 112 and configured for positioning over an associate ear of the user. Each earcup 114, 116 includes a respective circumaural foam cushion/seal 118, 120. Headset 112 includes an ambient microphone 122, 124 associated with each earcup 114, 116, respectively, and configured to generate signals response to ambient sound. An internal microphone 126, 128 is associated with each earcup 114, 116, respectively, and configured to generate signals response to sound within its respective earcup. A driver or speaker 140, 142 is positioned within each earcup 114, 116, respectively, and configured to generate sound response to at least one of a communication signal (such as from a linked external radio, smartphone, music player, or similar device as described below) and the signal from a respective one of the ambient microphones 122, 124 to provide selective pass-through of ambient sounds or speech for situational awareness.

As also illustrated in FIG. 1, system 100 includes at least one processor 150 in communication with the ambient microphones 122, 124, the internal microphones 126, 128, and the driver/speakers 140, 142. The at least one processor 150 is programmed or otherwise configured to control the speakers 140, 142 to sequentially generate sound at each of a plurality of predetermined frequencies (in sequence), the sound increasing in sound pressure level (SPL) at each of the plurality of frequencies until receiving a signal responsive to user input, such as from a user-operable input device, such as keypad 160, volume control 162, or linked smartphone 180. Processor 150 then stores an SPL value for each of the plurality of frequencies associated with the signal from the user operable input in a memory 152 accessible by the at least one processor 150. Memory 152 may be implemented using onboard non-volatile memory and/or by removable non-transitory computer readable storage media, such as a flash drive/card, or similar device, and/or by a remotely located non-volatile memory or storage device such as contained within linked smartphone 180 or a similar device, for example. The data may be stored in any convenient format, such as Comma-Separated Values (CSV) or machine-readable JSON formats, for example, whether stored locally on-board the headset 110 or remotely on a linked mobile device 180 for subsequent retrieval, use, and historical storage.

The at least one processor 150 then compares each stored SPL value to a corresponding reference value to determine associated difference values and generates a signal indicative of effectiveness of the ITE hearing protection devices based on the difference values. The corresponding reference value may be provided by the manufacturer of the ITE HPDs, may be empirically determined using historical data from the particular user for a particular type of ITE HPD, may be determined using historical data from similarly situated users, or from a baseline insertion loss test performed by the user without having the ITE HPDs inserted, for example, and may vary by application and implementation. Similarly, the effectiveness determination may vary by application and implementation based on typical use scenarios for the ITE HPDs. For example, the effectiveness determination may categorize effectiveness into two or more categories, such as pass/fail, poor/adequate/excellent, or unacceptable/marginal/acceptable/good. The criteria for each category may also vary depending on the application and implementation. As one example, in a test using five (5) test frequencies, the following criteria were used to provide a signal indicative of bad/adequate/good effectiveness: Bad if two or more frequencies have SPL difference values of less than 20 dB; Adequate if only one low-frequency point (250 Hz or 500 Hz) has SPL difference of less than 20 dB, or no more than two frequencies have SPL difference of less than 30 dB; and Good if all frequencies have SPL difference of more than 30 dB. The signal indicative of the effectiveness may activate a visual, audio, and/or haptic alert to the user corresponding to the effectiveness category. In one embodiment, the signal activates a visual, audio, and haptic alert via linked smartphone 180. For embodiments that do not include a linked smartphone 180, an audio and/or haptic alert may be provided via speakers 140, 142 and/or a vibrating transducer (not shown).

In one or more embodiments, headset 110 may include a transceiver 170, such as a Bluetooth transceiver, to wirelessly communicate with a linked device, such as smartphone 180, for example. A linking/pairing button 172 may be used to initiate a connection as known by those of ordinary skill in the art. Headset 110 may also include an integrated communication microphone, such as boom microphone 174 connected to and extending from one of the earcups 114, 116 and configured to generate signals in response to user speech. Boom microphone 174 may be in communication with at least one of the speakers 140, 142, and in communication with processor 150. Alternatively, or in combination, boom microphone 174 may be directly or indirectly coupled to an input/output jack 176 for wired connection to an external device, such as a radio, smartphone 180, computer (not shown), etc. Similarly, Alternatively, or in combination boom microphone may be directly or indirectly coupled to wireless transceiver 170 to transmit signals associated with user speech to a wirelessly connected external device, such as a radio, smartphone 180, computer (not shown), etc. Headset 110 also includes a battery compartment configured to provide power from an associated single-use or rechargeable battery to various system components.

For purposes of illustration and brevity of description, system 100 includes various components or features that are redundant and may be omitted in various embodiments. For example, embodiments including transceiver 170 may omit wired input/output jack 176. Similarly, embodiments that include transceiver 170 and/or input/output jack 176 to connect to an external device 180 having a user interface with one or more user-operable inputs may omit a keypad 160 and/or volume control 162. Likewise, boom microphone 174 and removable computer readable storage media 152 may be omitted in some embodiments. Those of ordinary skill in the art may recognize various other configurations and combinations of the illustrated and described components suitable for particular applications and implements that are within the scope of the claimed subject matter but not explicitly illustrated or described.

FIG. 2 is a flowchart illustrating operation of a system or method for evaluating ITE HPD effectiveness. The algorithm, process, or software represented in FIG. 2 includes various steps, tasks, or functions that may be performed by one or more programmed microprocessors or controllers as previously describe, such as processor(s) 150 (FIG. 1) and/or processor(s) of a remote computer or device, such as smartphone 180 (FIG. 1) in cooperation with associated components and hardware of a testing system, such as system 100 (FIG. 1).

Process or control strategy 200 generally represents a high-level description of a method for testing earplugs positioned within respective ear canals of a user. Step 210 generally represents sequentially emitting a sound or tone at each of a plurality of predetermined testing frequencies from circumaural earcups of a headset configured to be worn by the user, the sound at each of the predetermined testing frequencies increasing from a lower sound pressure level to a higher sound pressure level. In various embodiments, step 210 may be performed automatically by the processor. Alternatively, step 210 may be performed in response to a signal from a user operable volume control. For example, the processor may generate a sound at a first frequency with near zero SPL and the user may operate a volume control or other input to increase volume of the sound until the user hears the sound as noted by the volume control remaining at a particular volume for a predetermined period of time, or by reversing from increasing volume control to decreasing volume control (and possibly reversing again as the user identifies the hearing threshold volume). In other embodiments, the processor may automatically increase the SPL until the user activates an input, such as a touch screen on a linked smartphone, or a button on the headset, for example.

Responsive to receiving a signal indicative of the user hearing the sound at each of the plurality of predetermined testing frequencies, step 212 represents storing a frequency-associated sound pressure level value in fixed or removable non-transitory computer readable storage media, which may include wirelessly transmitting the sound pressure level values to a remotely located memory or storage media, such as a smartphone memory (for example), in some embodiments. The processor(s) then compare the frequency-associated sound pressure level value for each of the plurality of frequencies to corresponding predetermined frequency-associated reference values as represented at step 214 and determine an effectiveness category or rating of the earplugs in attenuating sound for each frequency based on the comparing as represented at 216. The process also includes providing, by the headset, an indication of the effectiveness of sound attenuation of the earplugs based on an aggregate effectiveness for the predetermined testing frequencies as represented at 218. Step 218 may include providing at least one of a visual, audio, and haptic indication. The indication may be provided via the headset, and/or a linked device such as a smartphone, for example.

In one or more embodiments, the process may further include the processor(s) compensating an input audio signal received by at least one microphone of the headset based on the frequency-associated sound pressure level values for the plurality of frequencies as represented at 220, and generating an audio output signal applied to at least one speaker of the headset based on the compensated input audio signal as represented at 224. In various embodiments, compensating the input audio signal may include determining an equalization function based on the frequency-associated sound pressure level values for at least one of the plurality of frequencies as represented at 230, and applying the equalization function to sound received by at least one microphone of the headset as represented at 232. Block 224 may include generating an equalized sound signal for at least one speaker of the headset as represented at 234.

Figure 3:
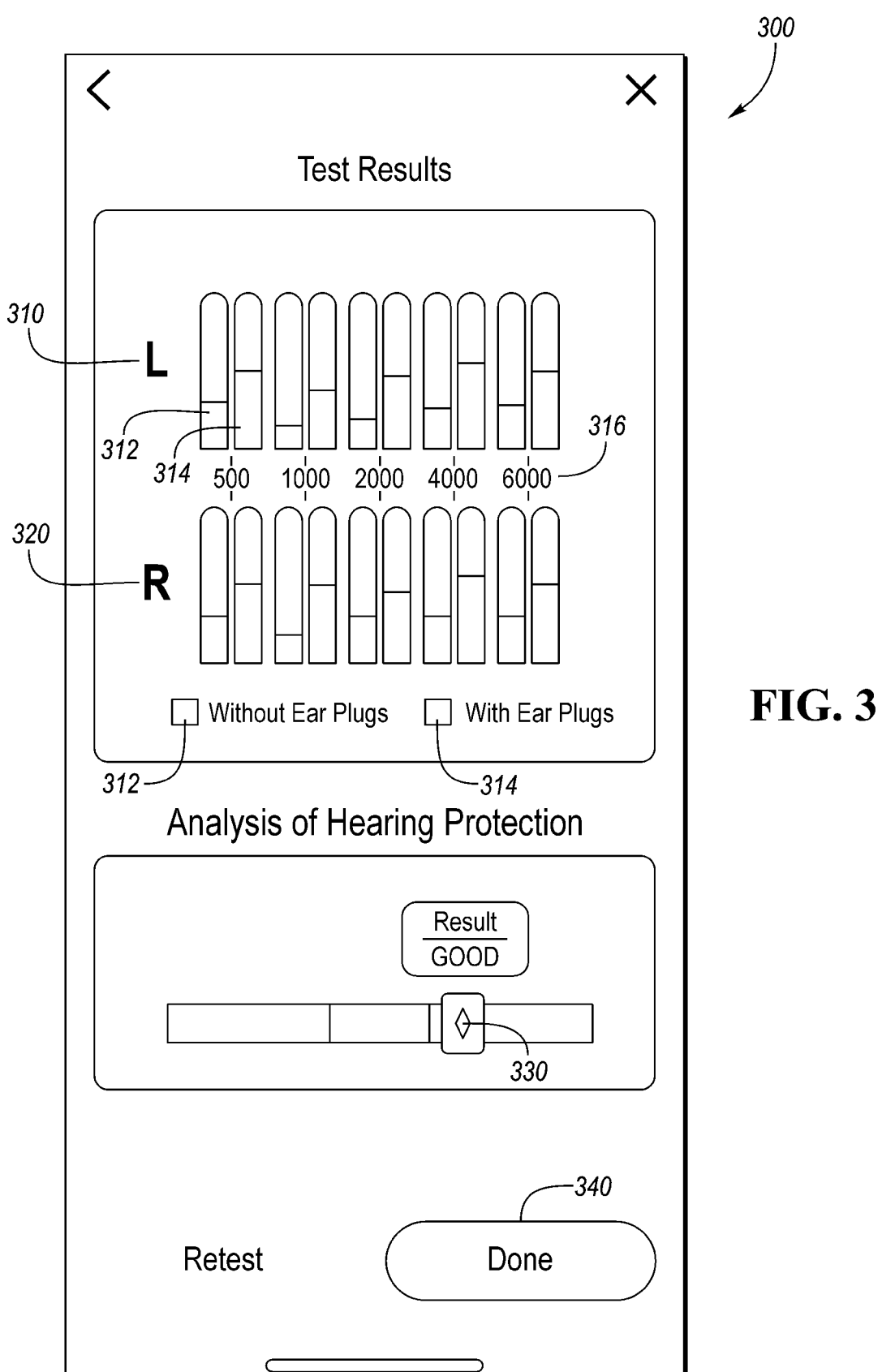
FIG. 3 is a representative user interface for a smartphone app displaying results of ITE HPD effectiveness testing.

FIG. 3 is a representative user interface for a smartphone app displaying results of ITE HPD effectiveness testing. User interface 300 may be implemented by a touch screen and/or may include one or more physical buttons, sliders, switches, etc. configured as user-operable inputs. User interface 300 may be used to display test results and/or obtain user input for control to initiate administration of the test and/or to provide input during the test as described herein. As illustrated in the representative embodiment of FIG. 3, user interface 300 provides bar graphs illustrating results of testing for a left ear 310 with bar 312 representing the SPL hearing threshold without earplugs (or alternatively another previously stored baseline reference value) and bar 314 representing the SPL hearing threshold with earplugs inserted. In the embodiment illustrated, the difference between the values represented by bars 312, 314 corresponds to the attenuation or protection provided at each of the test frequencies 316. In one embodiment, five (5) test frequencies are used (such as 500 Hz, 1 kHz, 2 kHz, 4 kHz, and 8 kHz). In another embodiment using five (5) test frequencies, frequencies of 250 Hz, 500 Hz, 1 kHz, 2 kHz, and 4 kHz are used. In other embodiments, up to twelve (12) frequencies may be used, such as 125 Hz, 250 Hz, 500 Hz, 750 Hz, 1 kHz, 1.5 kHz, 2 kHz, 3 kHz, 4 kHz, 6 kHz, 8 kHz, and 12 kHz, for example. The number of test frequencies and the selected frequencies may vary based on the particular application and implementation.

As also illustrated in FIG. 3, user interface 300 may include a visual indication 330 of the overall effectiveness of the ITE HPDs determined based on application-specific criteria as previously described. In this example, the test results indicate "GOOD" effectiveness based on the comparison of the SPL values with and without the ITE HPDs relative to the effectiveness determination criteria. User interface 300 may also include one or more control inputs to control test administration, interface configuration, etc. as generally represented at 340.

Figure 4:
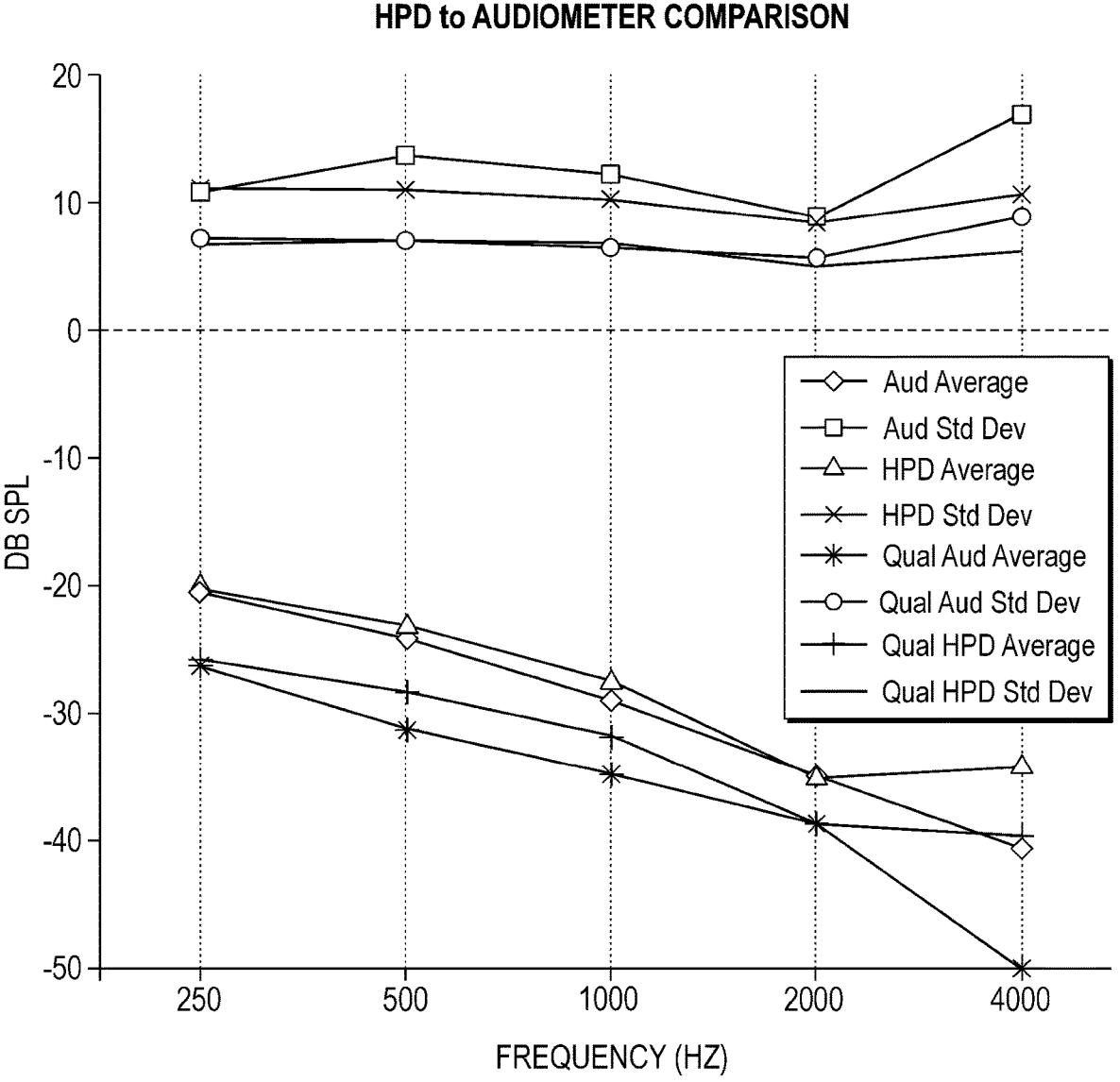
FIG. 4 illustrates performance of a representative system for evaluating ITE HPD effectiveness relative to audiometer measurements for a quiet ambient environment.
Figure 5:
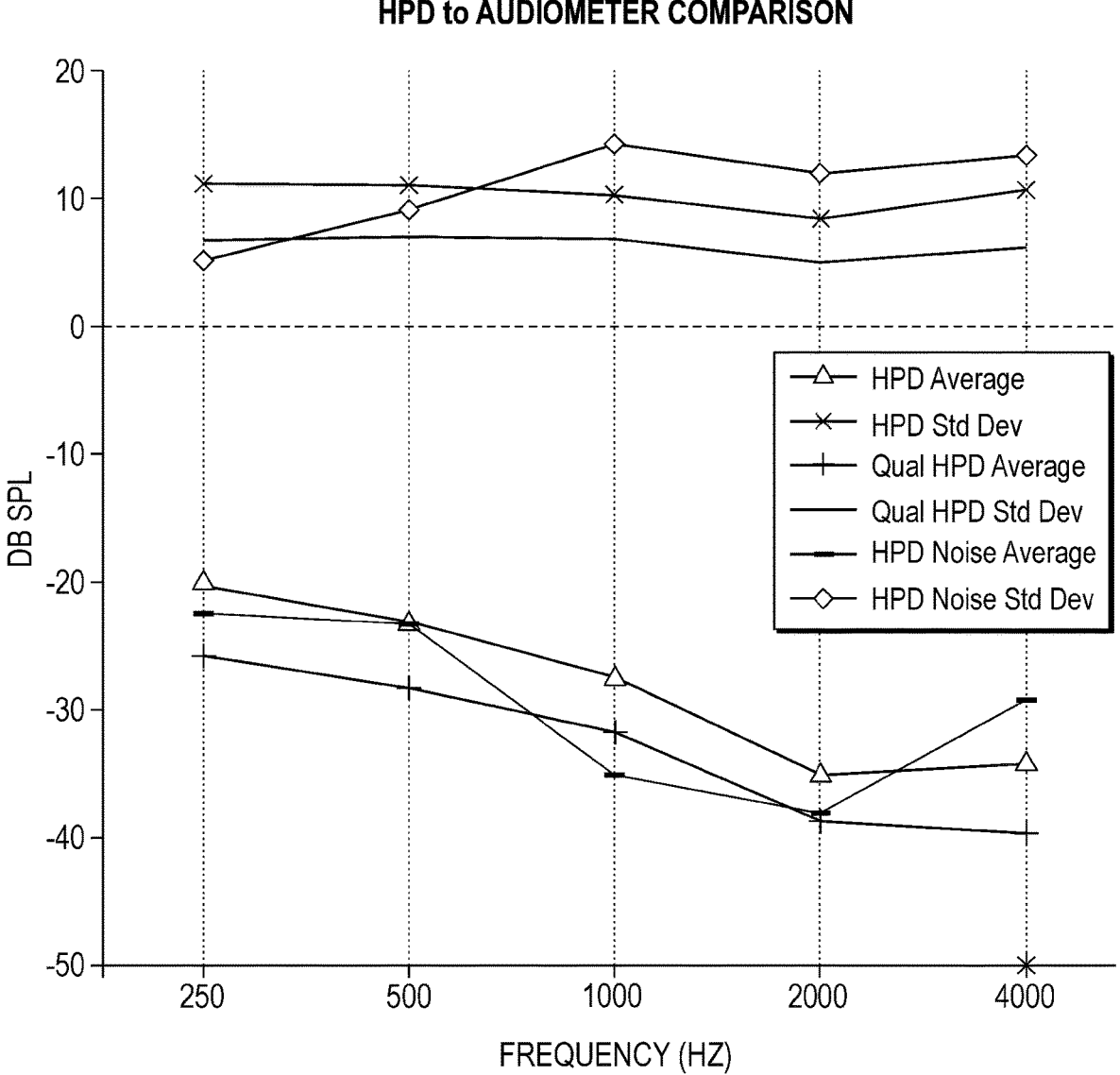
FIG. 5 illustrates performance of a representative system for evaluating ITE HPD effectiveness in a typical ambient environment with narrowband noise.

FIG. 4 illustrates performance of a representative system for evaluating ITE HPD effectiveness relative to audiometer measurements for a quiet ambient environment and FIG. 5 illustrates performance of the system in a typical ambient environment with narrowband noise. The narrow band noise used was white noise, A-Weighted, 2 kHz-4 kHz for 85-dBA, and was only present when wearing the HPD testing headset because the noise would otherwise drown out the audiometer data due to the nature of the on-the-ear headphones used in typical audiometer screening. The test subjects included seven (7) males of ages 29-69 years and three (3) females of ages 30-62 years. The testing protocol included the following steps: 1) Otoscopy examination and wax removal, if necessary; 2) tympanometry/immittance evaluation; 3) Don testing headset, run test at selected frequencies; 4) Doff testing headset, insert earplugs; 5) 1 kHz test to ensure some level of protection (Audiologist); 6) Don testing headset, complete test; 7) Don audiological headphones and measure hearing thresholds on audiometer; 8) Doff headphones, remove earplugs; 9) Don audiological headphones and retest hearing thresholds. For the ambient noise test illustrated in FIG. 5, steps 3) through 6) were repeated in the presence of the selected ambient noise.

As illustrated in the chart of FIG. 4, the overall performance of the testing headset is close to data provided by an audiogram. Using data from individuals with earplugs installed properly shows that the recorded levels are improved and that the standard deviation improves. In FIG. 5, the chart shows that the narrow band ambient noise affected the results for the corresponding frequencies. However, the small number of subjects and fit variability on those subjects may not be representative of a larger sample population or different noise profile. In either case, the criteria used to provide an indication of effectiveness was selected such that the indications provided by the testing headset data matched the indications provided by the audiometry measurements.

While the best mode has been described in detail, those familiar with the art will recognize various alternative designs and embodiments within the scope of the following claims. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments discussed herein that are described as less desirable than other embodiments or prior art implementations with respect to one or more characteristics are not outside the scope of the disclosure and may be desirable for particular applications.

What is claimed is:

1. A method for testing earplugs positioned within respective ear canals of a user, comprising:
emitting a sound at each of a plurality of predetermined testing frequencies from circumaural earcups of a headset configured to be worn by the user, the sound at each of the predetermined testing frequencies increasing from a lower sound pressure level to a higher sound pressure level;
responsive to receiving a signal indicative of the user hearing the sound at each of the plurality of predetermined testing frequencies, storing a frequency-associated sound pressure level value in a non-transitory computer readable storage device;
comparing, by a processor, the frequency-associated sound pressure level value for each of the plurality of frequencies to corresponding predetermined frequency-associated reference values;
determining, by the processor, effectiveness of the earplugs in attenuating sound for each frequency based on the comparing; and
providing, by the headset, an indication of the effectiveness of sound attenuation of the earplugs based on an aggregate effectiveness for the predetermined testing frequencies.

2. The method of claim 1 wherein the increasing from a lower sound pressure level to a higher sound pressure level is performed by the processor.

3. The method of claim 2 wherein the processor increases the sound pressure level in response to a signal from a user operable volume control.

4. The method of claim 3 wherein the signal indicative of the user hearing the sound corresponds to a signal from the user operable volume control.

5. The method of claim 4 wherein the signal indicative of the user hearing the sound corresponds to the signal from the user operable volume control, after increasing during a first period of time, either: a) remaining constant for a second period of time, or b) decreasing.

6. The method of claim 1 wherein providing the indication of the effectiveness of the sound attenuation includes providing at least one of a visual, audio, and haptic indication via the headset.

7. The method of claim 1 further comprising, by the processor:

determining an equalization function based on the frequency-associated sound pressure level values for at least one of the plurality of frequencies;

applying the equalization function to sound received by at least one microphone of the headset; and generating an equalized sound signal for at least one speaker of the headset.

8. The method of claim 1 further comprising, by the processor:

compensating an input audio signal received by at least one microphone of the headset based on the frequency-associated sound pressure level values for the plurality of frequencies; and generating an audio output signal applied to at least one speaker of the headset based on the compensated input audio signal.

9. The method of claim 1 wherein storing the frequency-associated sound pressure level values comprises wirelessly transmitting the sound pressure level values to a remotely located memory.

10. The method of claim 9 wherein the remotely located memory comprises a smartphone memory.

11. The method of claim 1 wherein the non-transitory computer readable storage device comprises removable storage media.

12. A system for evaluating effectiveness of in-the-ear (ITE) hearing protection devices after insertion into ear canals of a user, comprising:

a headband configured to extend around the head of the user;

a circumaural earcup connected to each end portion of the headband and configured for positioning over an associated ear of the user;

an ambient microphone associated with each ear cup and configured to generate signals responsive to ambient sound;

an internal microphone positioned within each ear cup and configured to generate signals responsive to sound within a respective earcup;

a speaker positioned within each ear cup and configured to generate sound responsive to at least one of a communication signal and the signal from a respective one of the ambient microphones; and at least one processor in communication with the ambient microphones, the internal microphones, and the speakers, the at least one processor programmed to:

control the speakers to sequentially generate sound at each of a plurality of frequencies, the sound increasing in sound pressure level (SPL) at each of the plurality of frequencies until receiving a signal responsive to user input;

store an SPL value for each of the plurality of frequencies associated with the signal from the user operable input in a memory accessible by the at least one processor;

compare each stored SPL value to a corresponding reference value to determine associated difference values; and generate a signal indicative of effectiveness of the ITE hearing protection devices based on the difference values.

13. The system of claim 12 further comprising a user operable input device configured to generate the signal responsive to the user input.

14. The system of claim 13 wherein the user operable input device comprises a wirelessly coupled smartphone.

15. The system of claim 13 wherein the user operable input device comprises a volume control positioned on one of the circumaural earcups.

16. The system of claim 12 wherein the user operable input device comprises a keypad positioned on one of the circumaural earcups.

17. The system of claim 12 further comprising a boom microphone extending from one of the circumaural earcups and configured to generate signals in response to user speech, the boom microphone in communication with the at least one processor.

18. The system of claim 17 further comprising an input/output jack in communication with the at least one processor and configured to receiving an external input/output plug and communicate signals between the at least one processor and an external device.

19. The system of claim 12 further comprising a transceiver in communication with the at least one processor and configured to wirelessly transmit the SPL values to a linked smartphone.

20. The system of claim 12 wherein the ambient microphones, the internal microphones, the speakers, and the at least on processor are positioned within at least one of the circumaural earcups.

* * * * *